(12) United States Patent
Gassa et al.

(10) Patent No.: US 11,325,922 B2
(45) Date of Patent: May 10, 2022

(54) PROCESS FOR THE PREPARATION OF CRISABOROLE IN A STABLE CRYSTAL FORM

(71) Applicant: OLON S.P.A., Rodano (IT)

(72) Inventors: Federico Gassa, Casaletto Lodigiano (IT); Lazzaro Feliciani, Casaletto Lodigiano (IT); Alberto Mazza, Casaletto Lodigiano (IT); Marco Quaroni, Casaletto Lodigiano (IT); Mara Sada, Segrate (IT); Giorgio Bertolini, Rodano (IT)

(73) Assignee: OLON S.P.A., Rodano (IT)

( * ) Notice: Subject to any disclaimer, the term of this patent is extended or adjusted under 35 U.S.C. 154(b) by 0 days.

(21) Appl. No.: 16/926,370

(22) Filed: Jul. 10, 2020

(65) Prior Publication Data

US 2020/0407377 A1  Dec. 31, 2020

Related U.S. Application Data (63) Continuation-in-part of application No. 16/771,567, filed as application No. PCT/EP2018/066899 on Jun. 25, 2018.

(30) Foreign Application Priority Data

Dec. 21, 2017  (IT) .................. 102017000148330

(51) Int. Cl.
 *C07F 5/02*  (2006.01)
(52) U.S. Cl.
 CPC .......... *C07F 5/025* (2013.01); *C07B 2200/13* (2013.01)
(58) Field of Classification Search
 CPC .................. C07F 5/025; C07B 2200/13
 See application file for complete search history.

(56) References Cited

U.S. PATENT DOCUMENTS

2015/0291629 A1  10/2015  Akama
2021/0002307 A1*  1/2021  Chen .................. C07F 5/027

FOREIGN PATENT DOCUMENTS

| WO | 2017093857 A1 | 6/2017 | |
|---|---|---|---|
| WO | WO-2017193914 A1 * | 11/2017 | ............ A61P 37/08 |
| WO | WO-2017203514 A1 * | 11/2017 | ............ A61K 31/69 |

OTHER PUBLICATIONS

U.S. Appl. No. 16/771,567 (Year: 2020).*
Akama, et al., "Discovery and structure-activity study of a novel benzoxaborole anti-flammatory agent (AN728) fo rthe potential topical treatment of psoriasis and atopic dermatitis", Bioorganic & Medicinal Chemistry Letters, Pergamon, Amsterdam, NL, vol. 19, No. 8, Apr. 15, 2009, pp. 2129-2132.
International Search Report and Written Opinion in corresponding International Application No. PCT/EP2018/066899 dated Nov. 2, 2018.

* cited by examiner

*Primary Examiner* — Rosalynd A Keys
(74) *Attorney, Agent, or Firm* — Arent Fox LLP

(57) ABSTRACT

The present invention relates to a process for the preparation of crisaborole of formula (I):

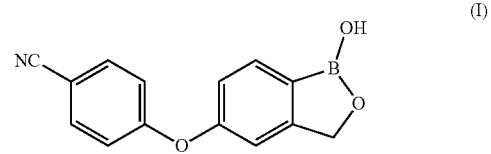

by preparing intermediates of formulas (II) and (III):

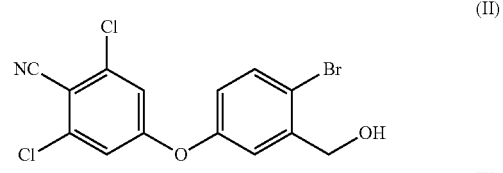

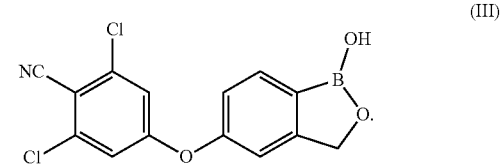

8 Claims, 7 Drawing Sheets

PROCESS FOR THE PREPARATION OF CRISABOROLE IN A STABLE CRYSTAL FORM

The present invention relates to a process for the synthesis of Crisaborole a non-steroidal medicament used for the treatment of atopic dermatitis in a high pure crystal stable form II.

TECHNICAL CONTEXT

Crisaborole is the international non-proprietary name of the compound 5-(4-cyanophenoxy)-1,3-dihydro-1-hydroxy-2,1-benzoxaborole having formula (I):

(I)

Crisaborole is the active ingredient of Eucrisa, a topical non-steroidal medicament approved by the FDA in the USA for the treatment of atopic dermatitis in patients from two years old. The molecule is currently undergoing clinical trials (phase II) for the treatment of (inter alia) psoriasis.

Crisaborole and its synthesis route were described and claimed for the first time in patent application WO2006/089067 by Anacor Pharmaceutical Inc.

The synthesis route used in WO2006/089067 (scheme) involves numerous steps, and the total yield is not very high, which makes the process expensive.

Scheme

It has surprisingly been found that by using a dichloroaryl intermediate of formula (V), as defined below, activated in the ortho position to the nitrile group by two electron-attracting groups, in particular two halogens, the reactions indicated in the 2-bromo-hydroxybenzaldehyde protection step (step 1) and the nucleophilic substitution reaction between the protected aldehyde and the fluorinated intermediate and subsequent reduction of the resulting product (step 2) can be replaced by a one-pot reaction, thus eliminating several steps.

The last purification step, which comprises dropwise addition of a 5:1 to 8:1, preferably 7:1 w/w, acetone:water mixture of the compound to water, followed by stirring at room temperature and filtration of the resulting product, is important to produce Crisaborole on an industrial scale in the highly pure and stable crystal form II. WO2017093857 describes three crystalline polymorphic forms of compound of formula-1 namely form-I, form-II and form-III.

The crystal form II is synthesized by the following steps:
1) crisaborole in solid free form is suspended in a mixture of water and an alcohol in a 1:1 volume ratio to produce a suspension which is stirred, subjected to centrifugal separation and dried, to provide the crystal form II in solid form. The alcohol is preferably methanol and the stirring and separation steps each are conducted at room temperature; alternatively 2) crisaborole in solid free form is dissolved in a positive solvent, and then an anti-solvent or reverse solvent is added thereto; the resultant mixture crystallized while being stirred, separated and dried, to produce the crystal form II, wherein crisaborole in free solid form is present in the positive solvent in a state that crisaborole is dissolved until the resultant mixture is clear or in a state in which crisaborole is completely dissolved, and the reverse solvent is added until solids are produced. The positive solvent includes, but is not limited to, alcohols, ketones, cyclic ethers, amides, and dimethyl sulfoxide, and the anti-solvent is preferably water, wherein: the alcohol solvent is isopropanol, the ketone solvent is acetone, the cyclic ether solvent is selected from tetrahydrofuran, and 1,4-dioxane, and the amide solvent is dimethylformamide; and both the stirring crystallizing step and the separating step are conducted at room temperature.

Following the procedure described in WO2017093857 (Example 5) Crisaborole is obtained in the pure crystal form II in a very small scale, in the order of a few milligrams (table 8).

The crystallization experiments with acetone and isopropyl alcohol (IPA), the solvents usually used in industrial scale up, were reproduced several times and crisaborole was obtained in a scale of grams in the crystal form I with impurities probably due to the presence of other polymorphic forms as reported below (example 12).

It was found that during the scale up of the process, due to the increase of the volumes, it is difficult to control the addition rate of anti-solvent to a solvent. If the anti-solvent is added in a single portion, the formation of form II is favorite, on the contrary if the anti-solvent is added portion wise with a controlled rate it is possible to obtain different polymorphic forms or mixtures and the procedure is not reproducible (see the comparative experiments reported in the experimental part).

Surprisingly, it was found that dissolving crude Crisaborole in a mixture of solvent and anti-solvent, (positive solvent and reverse solvent) in the ratio 5:1 to 8:1 w/w, preferably 7:1 w/w and adding the obtained solution directly to the anti-solvent (reverse solvent) the crystallization process can be controlled also during the scale up in order to selectively obtain pure form II.

In medicinal chemistry it is very important to perform a stable process which allows to obtain the desired API in a stable polymorphic form, that remains stable during all the manufacturing process. In this context, various federal agencies (FDA, EMA) require the appropriate description and characterization of the solid state of the API obtained at the end of the synthetic process.

DESCRIPTION OF THE INVENTION

The object of the present invention is a process for the preparation of Crisaborole of formula (I):
wherein said process comprises the following steps:
a) converting compound of formula (II):

to compound of formula (III):

in the presence of a tri ($C_1$-$C_4$) alkyl borate and a ($C_4$-$C_6$) alkyl lithium or aryl lithium, and subsequent acidification of the reaction medium; and b) converting the resulting compound of formula (III) to Crisaborole of formula (I) by catalytic hydrogenation.

The process of the invention can comprise a further step for the purification of Crisaborole, preferably by precipitating an acetone-water solution of the product in water.

The term ($C_4$-$C_6$) alkyl, as used herein, means a straight or branched alkyl chain having 4 to 6 carbon atoms such as n-hexyl, n-pentyl, n-butyl, isobutyl, isopentyl or tert-butyl.

The term ($C_1$-$C_4$) alkyl, as used herein, means a straight or branched alkyl chain having 1 to 4 carbon atoms such as methyl, ethyl, n-propyl, isopropyl, n-butyl or isobutyl.

The ($C_4$-$C_6$) alkyl lithium used in step a) of the process described above is preferably selected from butyl lithium and hexyl lithium.

The tri ($C_1$-$C_4$) alkyl borate used in step a) is preferably selected from trimethyl borate and triisopropyl borate.

Step a) is effected in a polar aprotic solvent such as cyclic or linear ethers or mixtures thereof, preferably tetrahydrofuran or methyl tetrahydrofuran, at a temperature ranging between −30° and −80° C.

The reaction medium is preferably acidified with acids such as hydrochloric acid, sulphuric acid, acetic acid and formic acid, in particular hydrochloric acid or acetic acid.

The catalytic hydrogenation of step b) is effected with palladium or platinum catalysts supported on carbon, barium sulphate or barium carbonate, such as 5% palladium on carbon, in a solvent such as ether, alcohol or water or in mixtures, at a temperature ranging between 0° and 50° C.

A further object of the invention is the process for the preparation of Crisaborole of formula (I) as described above, wherein compound of formula (II) is obtained by the following steps:

i) reacting compound of formula (IV):

wherein X is —COH or —CH$_2$OH, with compound of formula (V):

in the presence of an inorganic base, to give compound of formula (II) when X is —CH$_2$OH or compound of formula (VI) when X is —COH:

and ii) reducing compound of formula (VI) to give compound of formula (II).

The nucleophilic substitution reaction of step i) is effected in polar aprotic solvents such as toluene, dimethyl formamide, dimethylacetamide and methyl isobutyl ketone or mixtures thereof, preferably dimethyl formamide or dimethylacetamide, in the presence of inorganic bases such as alkali metal or alkaline-earth metal carbonates, in particular potassium carbonate.

The reaction is effected at a temperature ranging between 0° and 80° C.

The reduction reaction of step ii) is effected with reducing compounds such as KBH$_4$, NaBH$_4$ and LiBH$_4$ (potassium borohydride, sodium borohydride and lithium borohydride), preferably NaBH$_4$, in polar aprotic solvents such as THF, MeTHF, DMF and DMA (tetrahydrofuran, methyltetrahydrofuran, dimethylformamide, dimethylacetamide) or mixtures thereof, preferably tetrahydrofuran or methyltetrahydrofuran, at a temperature ranging between 0° and 50° C.

Another object of the invention is the process described above wherein compound of formula (IV), wherein X is —COH, is reacted with compound of formula (V), and steps i) and ii) are effected without isolating compound of formula (VI) (one-pot reaction).

Nucleophilic substitution reaction i) and reduction reaction ii), effected without isolating intermediate (VI), can be carried out by operating in solvents such as DMF, DMA and toluene or mixtures thereof, where necessary adding a phase-transfer catalyst such as tetrabutylammonium bromide, benzyl triethylammonium chloride, hexadecyl trimethylammonium bromide, tetrabutylammonium hydrogen sulphate and tetramethylammonium chloride (preferably tetrabutylammonium bromide).

Both reactions are effected at a temperature ranging between 0° and 120° C.

Compound of formula (IV) wherein X is —CH$_2$OH can be obtained by reducing compound of formula (IV) wherein X is —COH. Compound of formula (IV) wherein X is —COH is a commercial product.

The reduction of compound of formula (IV) wherein X is —COH can be effected in the presence of a reducing reagent such as potassium borohydride, sodium borohydride or lithium borohydride, preferably sodium borohydride, in polar aprotic solvents selected from tetrahydrofuran, dioxane, methyltetrahydrofuran, dimethyl formamide, dimethyl acetamide and toluene or mixtures thereof, preferably tetrahydrofuran or methyltetrahydrofuran.

The reaction is effected at a temperature ranging between 0 and 30° C.

Compound of formula V is a commercial product or obtainable by known processes from commercial products.

A further object of the invention is the reaction intermediates of formulae (II) and (III).

A further object of the invention is a process for the preparation of highly pure Crisaborole of formula (I) in the crystal form II:

said process comprising:
a) dissolving Crisaborole in a solvent mixture;
b) optionally filtering the solution;
c) adding dropwise the solution to water at a suitable temperature;
d) stirring the solution at room temperature;
e) filtering the obtained solid.

In step a) crude Crisaborole is dissolved in a solvent mixture comprising a polar aprotic solvent and water.

The polar aprotic solvent is selected from amides, ketones, nitriles, preferably ketones.

An acetone:water mixture in a ratio ranging from 5:1 to 8:1 w:w, preferably 7:1 w:w, is preferred.

The dissolution is effected at a temperature ranging between 0° and 80° C., preferably 20° and 70° C., advantageously at room temperature.

The solution obtained in step a) is optionally filtered to avoid the presence of any crystal form of Crisaborole.

The solution is added dropwise to water at 10-90° C., preferably at 20-80° C., advantageously at room temperature under stirring with a dripping speed between 1 l/h to 3 l/h, preferably 2 l/h.

Water is added in ratio 1 to 10 w/w with respect to the crude Crisaborole.

Step d) is carried out at 20-40° C., preferably at room temperature for 1-2 hours.

The crystals obtained are then isolated by filtration, washed with water and dried under vacuum for 6-18 h at 40° C.

The process is advantageous as it provides Crisaborole in a stable crystal form II in an industrial scale and also it allows an excellent removal of impurities from the final product, particularly those deriving from the hydrogenation step. The product resulting from said purification step has an X-ray diffraction spectrum (at Cu Kα wavelength) as reported in the annexed Figures. In particular, pure crisaborole form II is obtained, characterized by at least one of an XRD pattern having peaks at 16.5, 17.5, 20.9, 21.5, 22.5, and 28 degrees two-theta, ±0.2 (copper Kα wavelength) or a DSC scan showing a broad and small endotherm in the range of about 142° C. to about 145° C.

The process for the preparation of Crisaborole disclosed in WO2006/089067, and in *Bioorg. Med. Chem. Lett:* 19 (2009) 2129-2132 by the same authors, involves five chemical steps and a total yield of 32% (mean values of the methods described), and involves lengthy reactions, with hot treatments (100° C.). The processing of the intermediates involves distillations to dryness of large amounts of solvent, which are expensive and not very safe. No less than four chemical steps (aldehyde protection and alkylation, followed by deprotection and reduction) are required to obtain the key intermediate, and although they produce fairly good yields, they are lengthy and expensive.

In a preferred embodiment, the process of the invention, starting from 2-bromo-5-hydroxybenzaldehyde or the corresponding alcohol (2-bromo-5-hydroxy phenylmethanol), enables the key intermediate (4-(4-bromo-3-(hydroxymethyl)phenoxy) -2,6-dichlorobenzonitrile) to be prepared without isolating intermediates, operating at room temperature. The product is isolated by simple filtration after adding water as antisolvent to the reaction mixture. This is possible due to the addition of two chlorine atoms to 4-fluoro benzonitrile, which activate the aromatic nucleophilic substitution reaction. The two chlorine atoms are then removed to obtain Crisaborole by reduction. Despite the addition of this step, the process of the invention only consists of three steps, as against five. The total yield is higher (74% vs. 32%), the operating conditions are milder, and the processes are simpler and safer.

EXAMPLES

Example 1

Synthesis of 4-bromo-3-(hydroxymethyl)phenol (Compound of Formula (IV) Wherein X is —CH$_2$OH)

2-Bromo-5-hydroxy benzaldehyde (compound of formula IV wherein X is —COH) (20.1 g, 100 mmol) was dissolved in THF (80 mL), and the solution was cooled to 0-5° C. A solution of NaBH$_4$ (1.9 g, 50 mmol) in water (10 mL, stabilised with NaOH) was added in 30 min. The solution was stirred for a further 30 min. Acetone (25 mL) was added dropwise to the solution in 30 min. Water (50 mL) was then added, and THF was distilled off. The residual oil was extracted with AcOEt (200 mL). The organic phase was washed with saline solution (50 mL), then AcOEt was distilled off. The resulting solid was treated at 50° C. with 50 mL of toluene, and the suspension cooled to 20° C. The solid was filtered and dried at 65° C. to obtain the title compound as a white solid (18.6 g, 91%).

$^1$H-NMR; 300 MHz, DMSO-d$_6$. δ 9.64 (brs, 1H), 7.27 (d, 1H), 7.01 (d, 1H), 6.60 (dd, 1H), 5.37 (brs, 1H), 4.41 (s, 2H).

Example 2

Synthesis of 4-(4-bromo-3-(hydroxymethyl)phenoxy)-2,6-dichlorobenzonitrile of Formula (II)

4-Bromo-3-(hydroxymethyl)phenol (5.0 g, 25 mmols) (compound of formula (IV) wherein X is —CH$_2$OH) was dissolved in DMF (30 mL). 2,6 Dichloro-4 fluorobenzonitrile (4.9 g, 26 mmol) (compound of formula (V)) and K$_2$CO$_3$ (3.9 g, 28 mmols) were added, and the suspension was stirred for 5 hours. Water (100 mL) was added, and compound of formula (II) was collected as a white solid by filtration (7.3 g, 19.6 mmols, 80%).

$^1$H-NMR; 300 MHz, DMSO-d$_6$. δ 7.65 (d, 1H), 7.30 (d, 1H), 7.06 (dd, 1H), 5.55 (t, 1H), 4.49, (d, 2H).

$^{13}$C-NMR; 300 MHz, DMSO-d$_6$. δ 161.8, 153.6, 144.4, 139.1, 134.4, 120.9, 102.1, 118.0, 117.4, 114.0, 107.5, 62.8.

Example 3

Synthesis of 2,6-dichloro-4-((1-hydroxy-1,3-dihydrobenzo[c][1,2]oxaborol-5-yl)oxy)benzonitrile of Formula (III)

4-(4-Bromo-3-(hydroxymethyl)phenoxy)-2,6-dichlorobenzonitrile of formula (II) (50.0 g, 164 mmols), 3,4-dihydropyran (34.9 g, 415 mmols) and pyridinium p-toluenesulphonate (2.0 g, 8 mmols) were stirred in THF for 24 hours. TiPrOB (49.2, 262 mmols) was added, and the solution was cooled to −78° C. A hexyllithium 2.3 molar solution in hexane was added dropwise in 40 min., and the final mixture was stirred at said temperature for 90 min. The solution was heated to room temperature and kept under stirring at said temperature for a total of 2 hours. THF was then distilled off 100 mL of 6N HCl was added slowly, and the suspension was stirred for 16 hours. EtOH (400 mL) was added, and compound of formula (III) was obtained by filtration (36.0 g, 112 mmols, 84%).

$^1$H-NMR; 300 MHz, DMSO-d$_6$. δ 9.25 (s, 1H), 7.82 (d, 1H), 7.33 (s, 2H), 7.23 (d, 1H), 7.15 (dd, 1H), 4.98 (s, 2H)

$^{13}$C-NMR; 300 MHz, DMSO-d$_6$. δ161.8, 157.2, 156.4, 139.1, 133.2, 119.6, 118.4, 114.1, 113.7, 107.5, 70.1

Example 4

Synthesis of Crisaborole of Formula (I)

2,6-Dichloro-4-((1-hydroxy-1,3-dihydrobenzo[c][1,2]oxaborol-5-yl)oxy)-benzonitrile (10.0 g, 31 mmols) and KOH (5.0 g, 84 mmols) were suspended in a mixture of ethanol (100 mL) and water (100 mL). 5% Pd on carbon (1.0 g) was then added, and the mixture was placed under hydrogen atmosphere at 1-5 ATM. The reaction was completed after 1 h, and the catalyst was filtered off 37% Hydrochloric acid was added to the filtered solution to obtain a pH of less than 2. The solution was concentrated under vacuum at 50 mL, and a white solid precipitated. The suspension was cooled to room temperature and stirred for 1 hour. Crisaborole was then isolated by filtration (7.0 g, 28 mmol, 90%).

Example 5

Synthesis of 4-(4-bromo-3-(hydroxymethyl)phenoxy)-2,6-dichlorobenzonitrile (One-Pot Reaction in DMA) of Formula (II)

2-Bromo-5-hydroxybenzaldehyde (30.0 g, 149 mmols) and 2,6-dichloro-4-fluorobenzonitrile (30.0 g, 158 mmols) were dissolved in DMA (130 mL), and K$_2$CO$_3$ (27.0 g, 195 mmols) was added to the solution. The reaction was maintained at 20-30° C. for 3-6 hours, after which a solution of NaBH$_4$ (2.0 g, 53 mmols) in water (20 mL, stabilised with 5% NaOH) was added in 20 min. The solution was kept under stirring for a further 30 min., then water (500 mL) was added. The solution was kept under stirring for 1 hour, and the title product was isolated as a white solid by filtration (54.6 g, 146 mmols, 98%).

Example 6

Synthesis of 4-(4-bromo-3-(formylphenoxy)-2,6-dichlorobenzonitrile of Formula (VI)

-continued

2-Bromo-5-hydroxy benzaldehyde (30.0 g, 149 mmols) was dissolved in DMF (120 mL), 2,6-dichloro-4-fluorobenzonitrile (30.0 g, 158 mmols) and $K_2CO_3$ (27.0 g, 195 mmols) were added to the solution, and the suspension was stirred for 1-4 h, maintaining the temperature under 30° C. Water (300 mL) was added, and a white solid was collected by filtration and washing with water (100 mL). (54.2 g, 146 mmol, 97%).

$^1$H-NMR; 300 MHz, CDCl$_3$. δ 10.33 (s, 1H), 7.76 (d, 1H), 7.60 (d, 1H), 7.22 (dd, 1H), 6.98 (s, 2H)

$^{13}$C-NMR; 300 MHz, CDCl$_3$. δ 190.5, 160.6, 153.7, 139.9, 136.1, 135.2, 127.3, 123.2, 117.3, 113.2, 109.1.

Example 7

Synthesis of 4-(4-bromo-3-(hydroxymethyl)phenoxy)-2,6-dichlorobenzonitrile of Formula (II)

4-(4-Bromo-3-formylphenoxy)-2,6-dichlorobenzonitrile (77.8 g, 210 mmols) was dissolved in THF (365 mL), and the solution was cooled to 0-5° C. A solution of NaBH$_4$ (2.7 g, 71 mmols) in water (25 mL, stabilised by NaOH) was added in 1 hour. The solution was kept under stirring for a further 30 min. Acetone (25 mL) was added dropwise in 30 min., then water (150 mL) was added. THF was distilled off, and a solid precipitate was obtained. The suspension was cooled to room temperature, and the product was isolated as a white solid by filtration (77.6 g, 208 mmols, 98%). The crude product was suspended in toluene (320 mL) and placed under reflux for 30 minutes. The solution was slowly cooled to room temperature, and the pure white solid was recovered by filtration (75.3 g, 95%).

Example 8

Synthesis of 4-(4-bromo-3-(hydroxymethyl)phenoxy)-2,6-dichlorobenzonitrile of Formula (II) (Phase-Transfer Conditions)

4-(4-Bromo-3-formylphenoxy)-2,6-dichlorobenzonitrile (15.0 g, 40 mmols) and TBAB (0.15 g, 0.5 mmols) were suspended in toluene (140 mL), and the solution was heated to 45-50° C. A solution of NaBH$_4$ (0.6 g, 16 mmol) in water (6 mL, stabilised with NaOH) was added in 10 min. The solution was kept under stirring for a further 60 min. Acetic acid (3.6 g) was added dropwise in 30 min., and the mixture was then kept under stirring for 30 min. The suspension was heated to 80° C., and the aqueous phase was separated. 70 mL of toluene was distilled off, and the solution was cooled to room temperature. The product was isolated as a white solid by filtration (13.0 g, 35 mmols, 88%).

Example 9

Synthesis of 4-(4-bromo-3-(hydroxymethyl)phenoxy)-2,6-dichlorobenzonitrile of Formula (II) (Reaction in Phase-Transfer Conditions)

2-Bromo-5-hydroxy-benzaldehyde (10.0 g, 50 mmols), 2,6-dichloro-4-fluoro benzonitrile (9.9 g, 52 mmols), $K_2CO_3$ (8.9 g, 64 mmols) and TBAB (1 g, 0.3 mmols) were suspended in toluene (100 mL), and the solution was heated to 70° C. for 24 hours. The solution was cooled to room temperature and washed twice with water (50 ml). A solution of NaBH$_4$ (0.65 g, 170 mmols) in water (15 mL) was added dropwise, and the solution was kept under stirring for a further 30 min. The solution was washed twice with water (50 mL) and concentrated to 40 mL. The solution was then cooled to room temperature, and the product was isolated as a white solid by filtration (16.6 g, 44 mmols, 88%).

Example 10

Purification of Crisaborole

Figure 1:
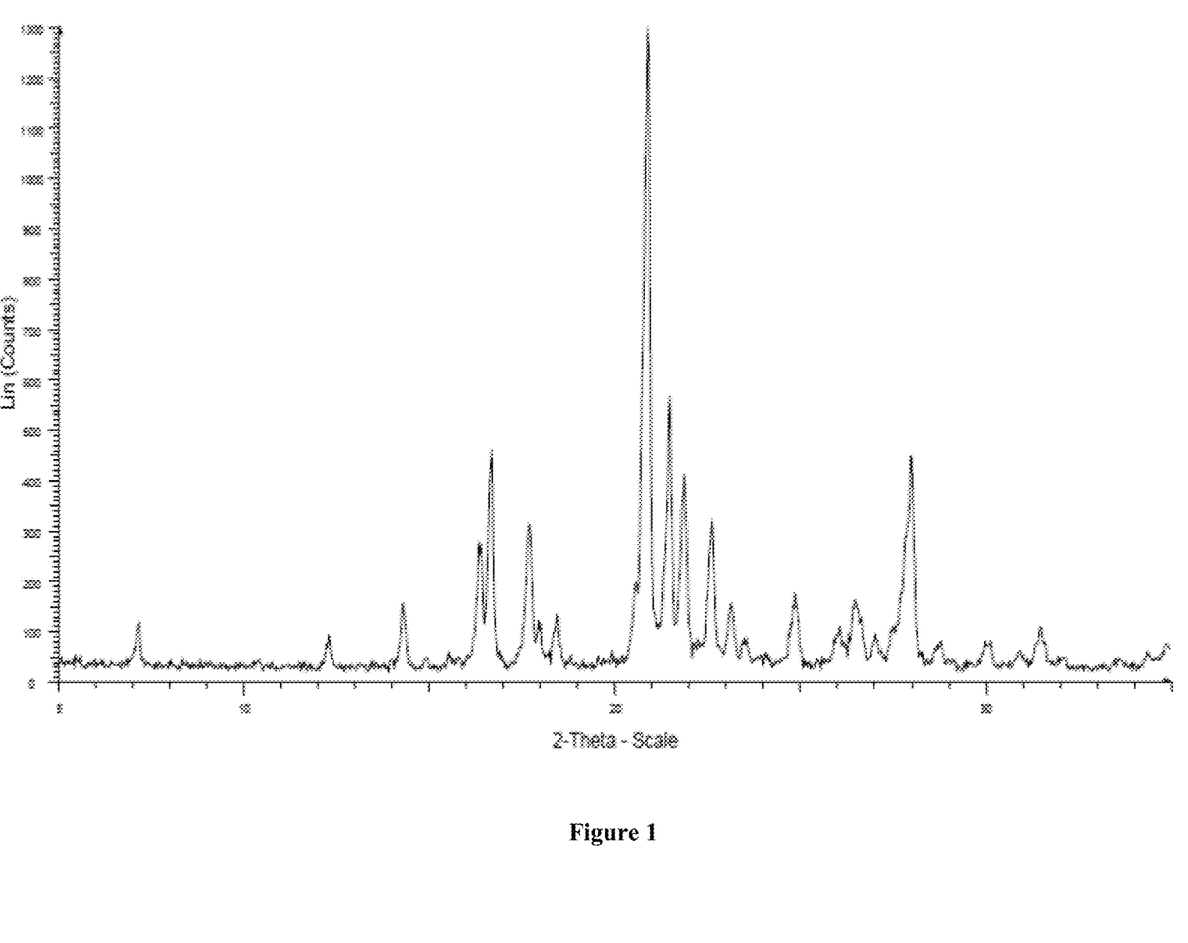
FIG. 1: An x-ray diffraction pattern of purified Crisaborole of Examples 10 and 11.
Figure 2:
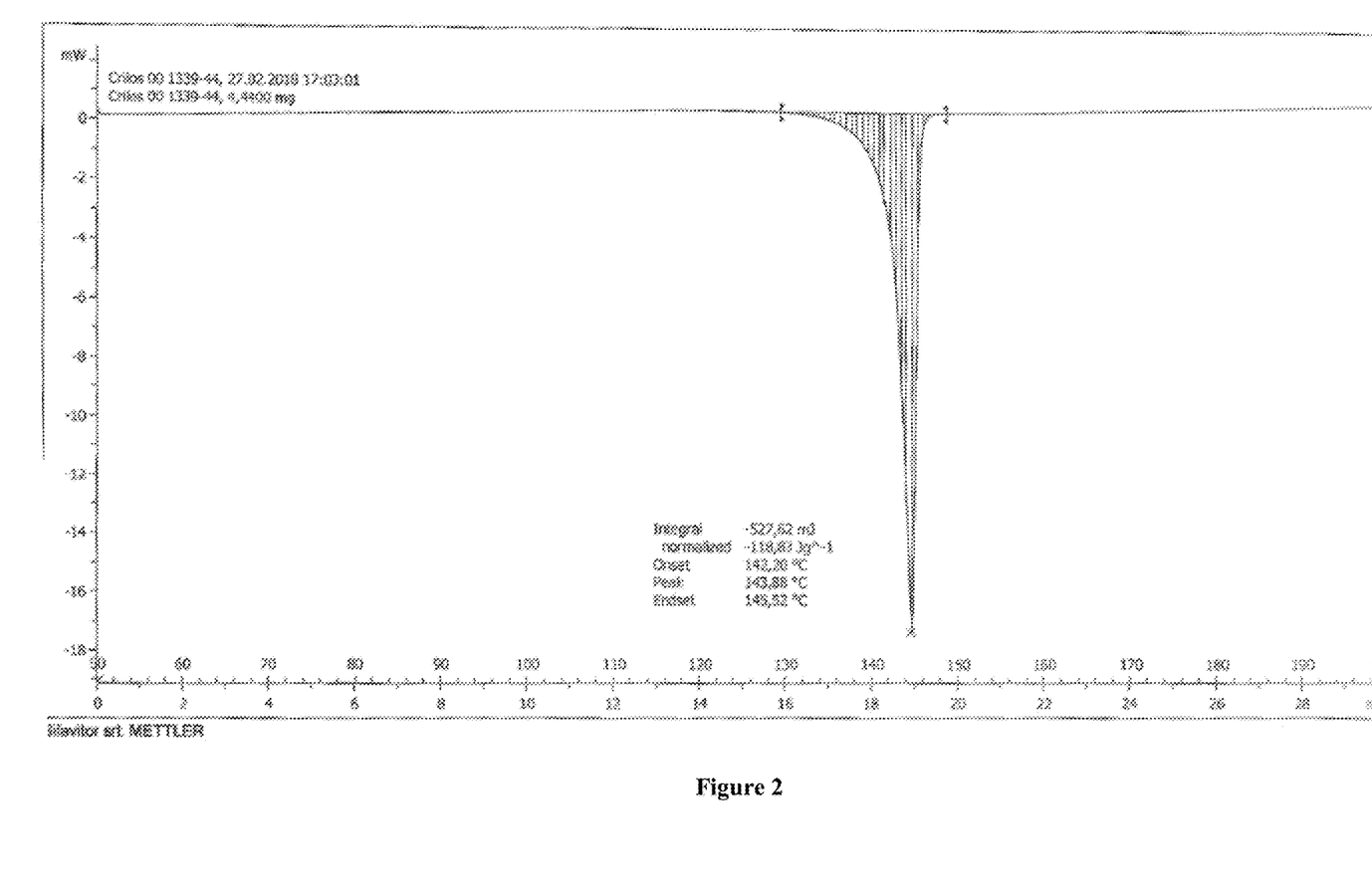
FIG. 2: A differential scanning calorimetry scan of purified Crisaborole of Examples 10 and 11.
Figure 3:
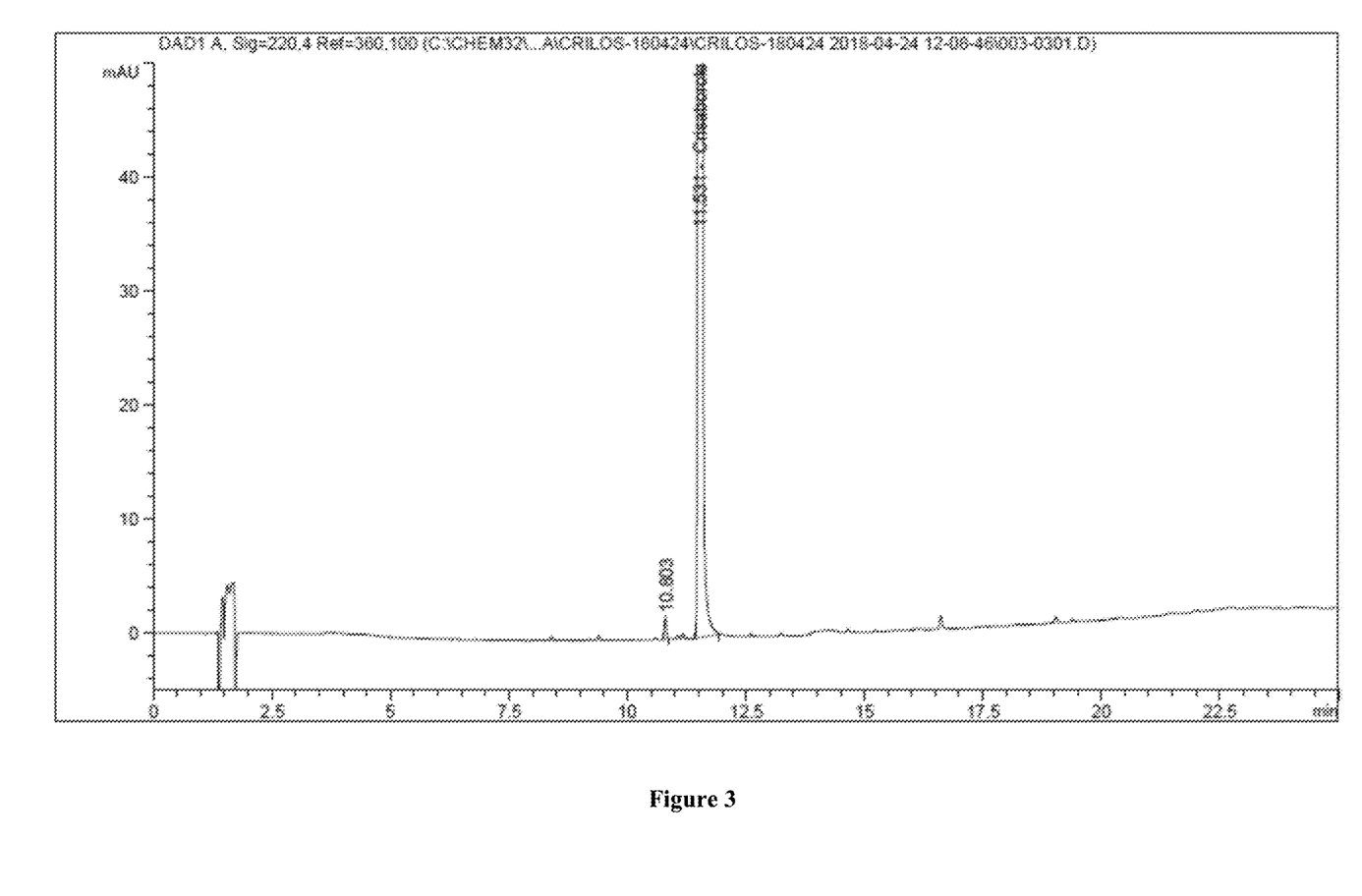
FIG. 3: A high performance liquid chromatogram of purified Crisaborole of Examples 10 and 11.

A Crisaborole (100 g) solution in a mixture of 350 g of acetone and 50 g of water was added dropwise to 1 liter of water at 25° C. during 30'. The resulting mixture was stirred for approx. 1-2 hrs. at room temperature, then filtered. Drying at 40° C. under vacuum yielded 96 g of product with chromatographic assay higher than 99.8%, having the X-ray diffraction spectrum (CuαK), the DSC and the HPLC as reported in the FIGS. 1, 2 and 3 respectively.

Example 11

Purification of Crisaborole

A Crisaborole (100 g) solution in a mixture of 350 g of acetone and 50 g of water was stirred at 60° C. added dropwise to 1 liter of water at 70-75° C. during 30'. When the addition is complete the suspension is cooled at room temperature, then filtered. Drying at 40° C. under vacuum yielded 97 g of product with chromatographic assay higher than 99.8%, having the X-ray diffraction spectrum (CuαK), the DSC and the HPLC as reported in the FIGS. 1, 2 and 3 respectively.

Example 12

Purification of Crisaborole Using Procedure Reported in WO2017093857

Example 5

Batch No. 1359-93A

Crisaborole (15.0 g) was dissolved in IPA (155.6 g, 198 ml) at room temperature for 30'. Water (297 g, 297 ml) was added dropwise in 60' and the mixture was stirred for 5 days. Pure crisaborole (12.3 g) was filtered and dried at r.t.

Batch No 1359-93B

Crisaborole (15.0 g) was dissolved in acetone (73.2 g, 93.4 ml) at room temperature for 30'. Water (92.6 g, 92.6 ml) was added dropwise in 40' and the mixture was stirred for 5 days. Pure crisaborole (12.2 g) was filtered and dried at r.t.

Study of the Crystalline Phase of Crisaborole Batches N°1359-93A and N° 1359-93B

The samples were examined with vertical goniometer BRUKER D5005 diffractometer at the following diffraction conditions: scanning step of 0.030° with counting time of 2 seconds/step in the angular range 5-35°. Use was made of copper Kα radiation (30 kV, 40 mA), graphite monochromator, room temperature, in a Si monocrystalline low background sample holder.

Figure 4:
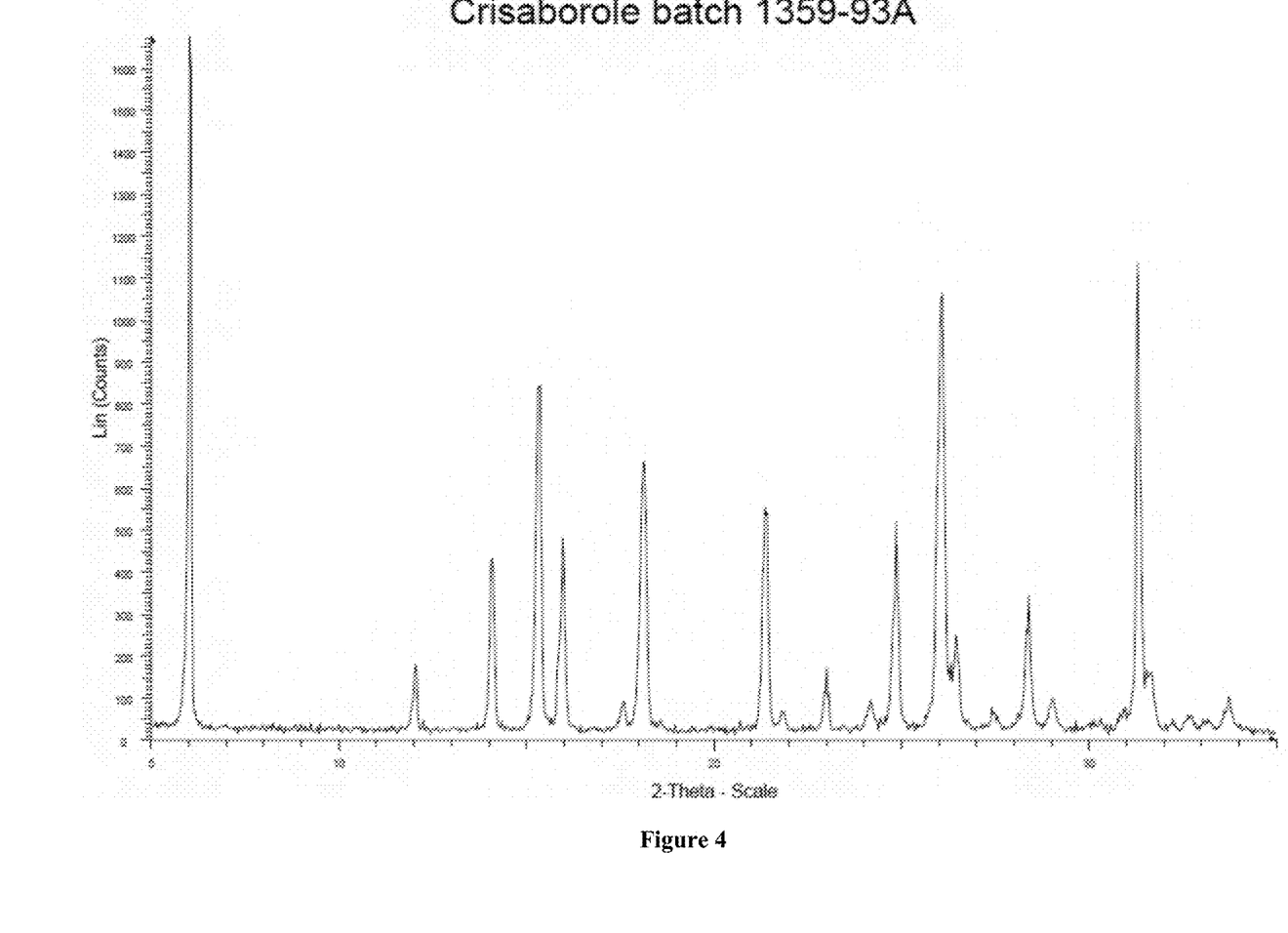
FIG. 4: An x-ray diffraction pattern of the purified product of Crisaborole batch 1359-93A.
Figure 5:
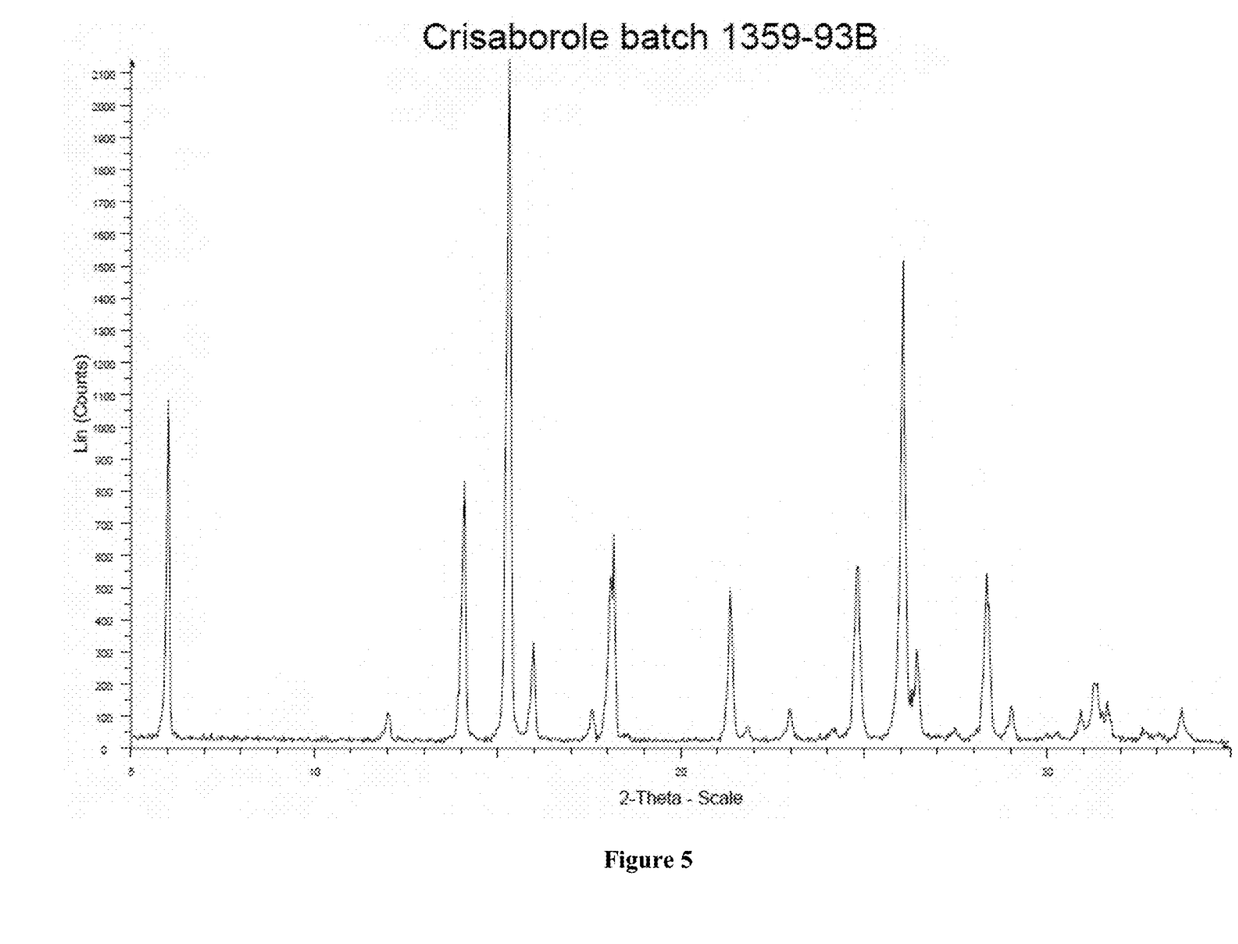
FIG. 5: An x-ray diffraction pattern of the purified product of Crisaborole batch 1359-93B.
Figure 6:
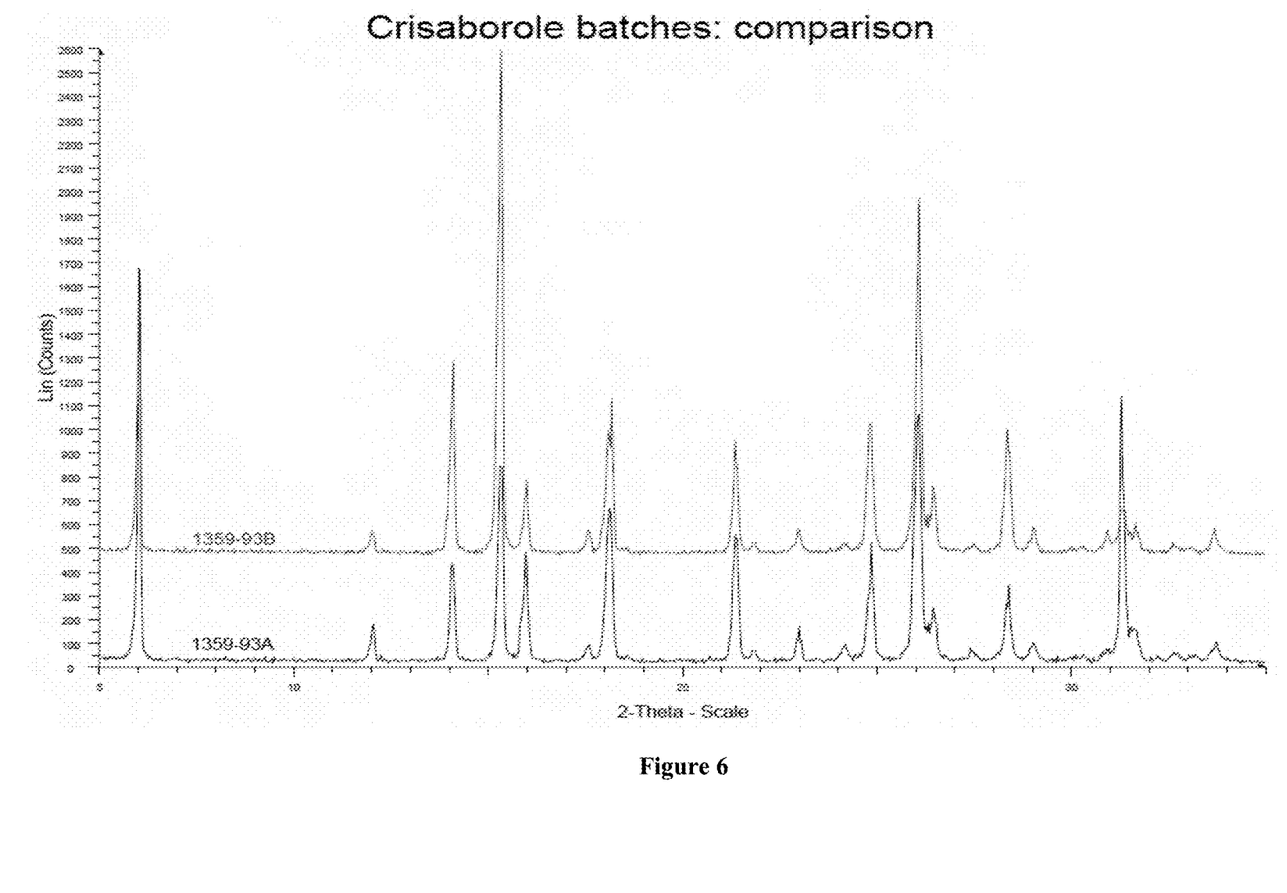
FIG. 6: An x-ray diffraction pattern comparing the purified product of Crisaborole batches 1359-93A and 1359-93B.

The diffraction patterns of the Crisaborole samples batch no 1359-93A and no 1359-93B are reported in FIGS. 4 and 5 and compared in FIG. 6. They are both well crystalline and present the same peak positions and intensities, suggesting the presence of the same crystalline form.

Figure 7:
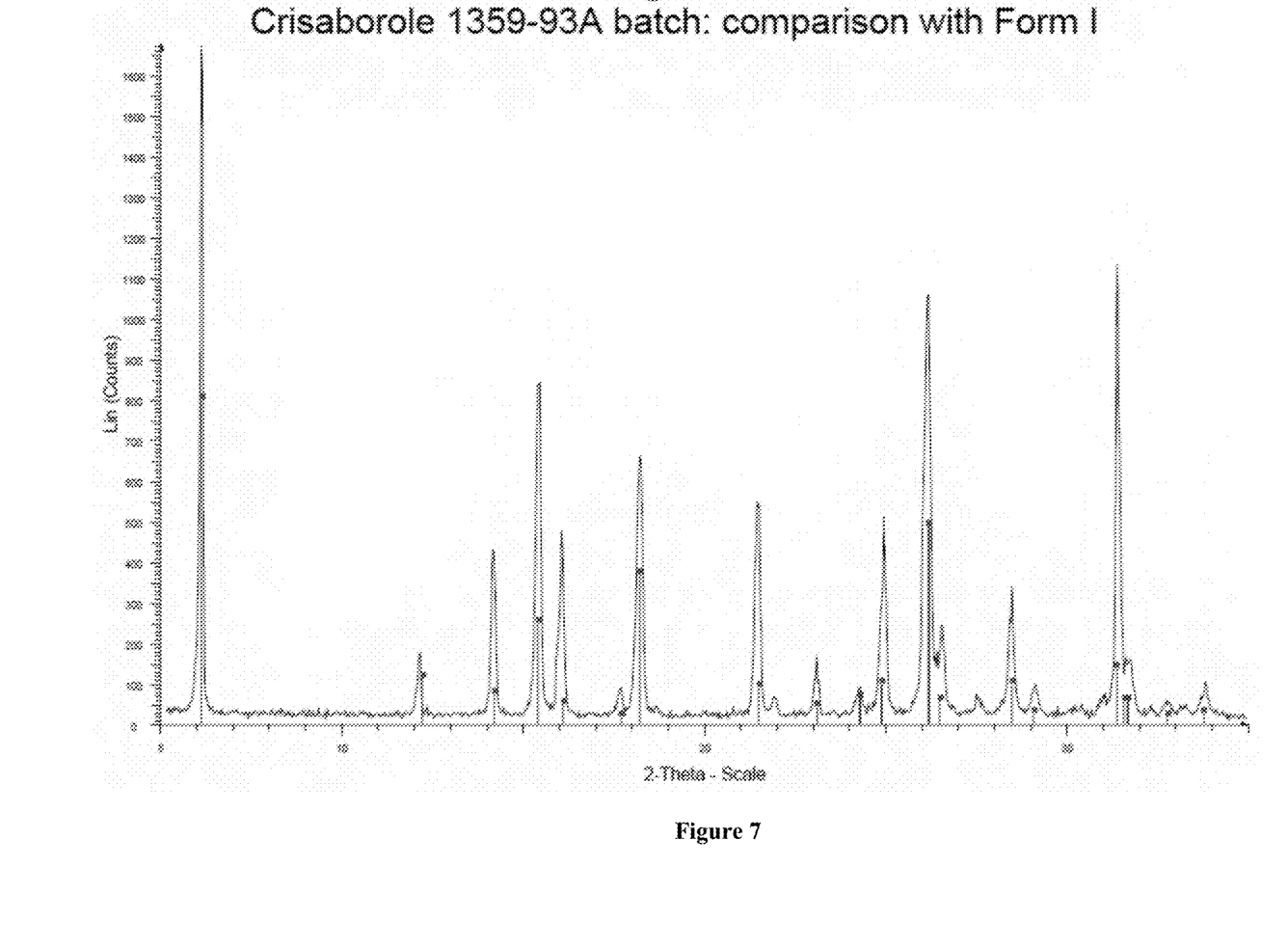
FIG. 7: An x-ray diffraction pattern comparing the purified product of Crisaborole batch 1359-93A and Crisaborole Form I.

In FIG. 7, as an example, the pattern of the sample 1359-93A is compared with the peaks of Crisaborole Form 1 showing a good agreement. The two small peaks (at about 22 and 27.5°) not equivalent to the peaks of Form I could be attributed to traces of a different polymorph (Form II or III) or to some impurity phase.

The invention claimed is:

1. A process for the purification of Crisaborole of formula (I)

said process comprising:
a) dissolving crude Crisaborole in a solvent mixture;
b) optionally filtering the solution;
c) adding dropwise the solution to water at a suitable temperature;
d) stirring the solution;
e) filtering the obtained solid,
wherein step a) is carried out in an acetone:water mixture of 5:1 to 8:1 w/w.

2. The process according to claim 1 wherein step a) is carried out in an acetone:water mixture of 7:1 w/w.

3. The process according to claim 1, wherein step a) is carried out at 10-80° C.

4. The process according to claim 1, wherein step c) is carried out at 10-90° C.

5. The process according to claim 1, wherein in the step c) water is used in ratio 1 to 10 w/w with respect to the crude Crisaborole.

6. The process according to claim 1 wherein step d) is carried out at 20-40° C., for 1-2 hours.

7. The process according to claim 1 wherein Crisaborole is obtained in form II characterized by at least one of
an XRD pattern having peaks at 16.5, 17.5, 20.9, 21.5, 22.5, and 28 degrees two-theta, ±0.2 at the copper Kα radiation or
a DSC scan showing a broad and small endotherm in the range of about 142° C. to about 145° C.

8. The process according to any one of the preceding claims, wherein in the step c) the solution is added with a dropping rate between 1 l/h to 3l/h.

* * * * *